(12) United States Patent
Romonti

(10) Patent No.: US 8,997,295 B1
(45) Date of Patent: Apr. 7, 2015

(54) SMART BELT TOOTH BRUSH

(71) Applicant: Justin Romonti, Desplaines, IL (US)

(72) Inventor: Justin Romonti, Desplaines, IL (US)

( * ) Notice: Subject to any disclaimer, the term of this patent is extended or adjusted under 35 U.S.C. 154(b) by 0 days.

(21) Appl. No.: 13/960,368

(22) Filed: Aug. 6, 2013

(51) Int. Cl.
*A46B 13/02* (2006.01)
*A61C 17/22* (2006.01)
*A61C 17/26* (2006.01)

(52) U.S. Cl.
CPC ..................................... *A61C 17/26* (2013.01)

(58) Field of Classification Search
CPC .......... A46B 7/06; A46B 13/00; A46B 13/02; A61C 17/22; A61C 17/222; A61C 17/24; A61C 17/26
USPC .................................................. 15/22.1, 22.3
See application file for complete search history.

(56) References Cited

U.S. PATENT DOCUMENTS

| 4,313,237 | A | | 2/1982 | Smith |
| 4,320,774 | A | | 3/1982 | Rogers |
| 4,603,448 | A | * | 8/1986 | Middleton et al. ............. 15/22.1 |
| 5,864,911 | A | | 2/1999 | Arnoux et al. |
| 6,032,313 | A | * | 3/2000 | Tsang ............................ 15/22.1 |
| 7,346,954 | B2 | | 3/2008 | Weber et al. |
| 8,281,443 | B2 | | 10/2012 | Brown et al. |
| 8,298,342 | B2 | | 10/2012 | Haas et al. |
| 2010/0132140 | A1 | | 6/2010 | Diamond |

FOREIGN PATENT DOCUMENTS

DE  19842483  *  3/1999

* cited by examiner

*Primary Examiner* — Mark Spisich

(57) ABSTRACT

A teeth cleaning assembly includes a housing. A first wheel and a second wheel are each rotatably mounted to the housing. A belt is continuous and is positioned on the first and second wheels. The belt rotates the second wheel when the first wheel is rotated. A plurality of bristles is attached to the belt and extends away from the first and second wheels such that the bristles extend outwardly of the housing. A handle is attached to the housing and a motor is mounted within the handle. The motor is in mechanical communication with the first wheel. The motor rotates the first wheel when the motor is energized.

7 Claims, 6 Drawing Sheets

SMART BELT TOOTH BRUSH

BACKGROUND OF THE DISCLOSURE

Field of the Disclosure

The disclosure relates to teeth cleaning devices and more particularly pertains to a new teeth cleaning device for assisting a person in cleaning their teeth.

SUMMARY OF THE DISCLOSURE

An embodiment of the disclosure meets the needs presented above by generally comprising a housing. A first wheel and a second wheel are each rotatably mounted to the housing. A belt is continuous and is positioned on the first and second wheels. The belt rotates the second wheel when the first wheel is rotated. A plurality of bristles is attached to the belt and extends away from the first and second wheels such that the bristles extend outwardly of the housing. A handle is attached to the housing and a motor is mounted within the handle. The motor is in mechanical communication with the first wheel. The motor rotates the first wheel when the motor is energized.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
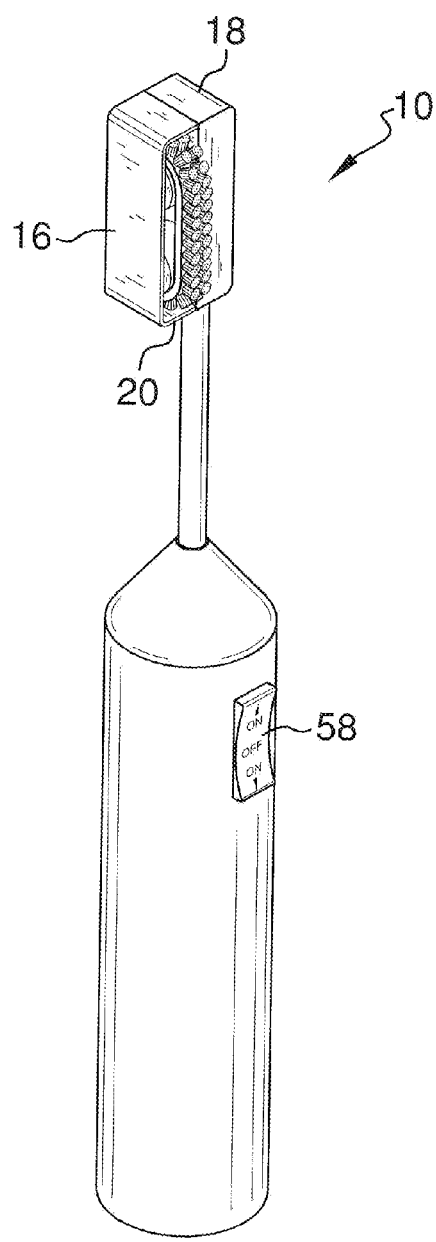
FIG. 1 is a left perspective view of a teeth cleaning assembly according to an embodiment of the disclosure.
Figure 2:
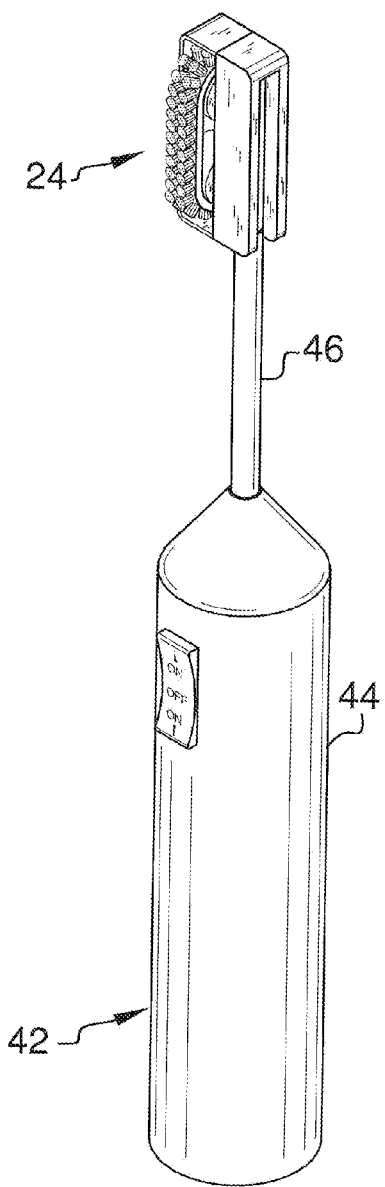
FIG. 2 is a right perspective view of an embodiment of the disclosure.
Figure 3:
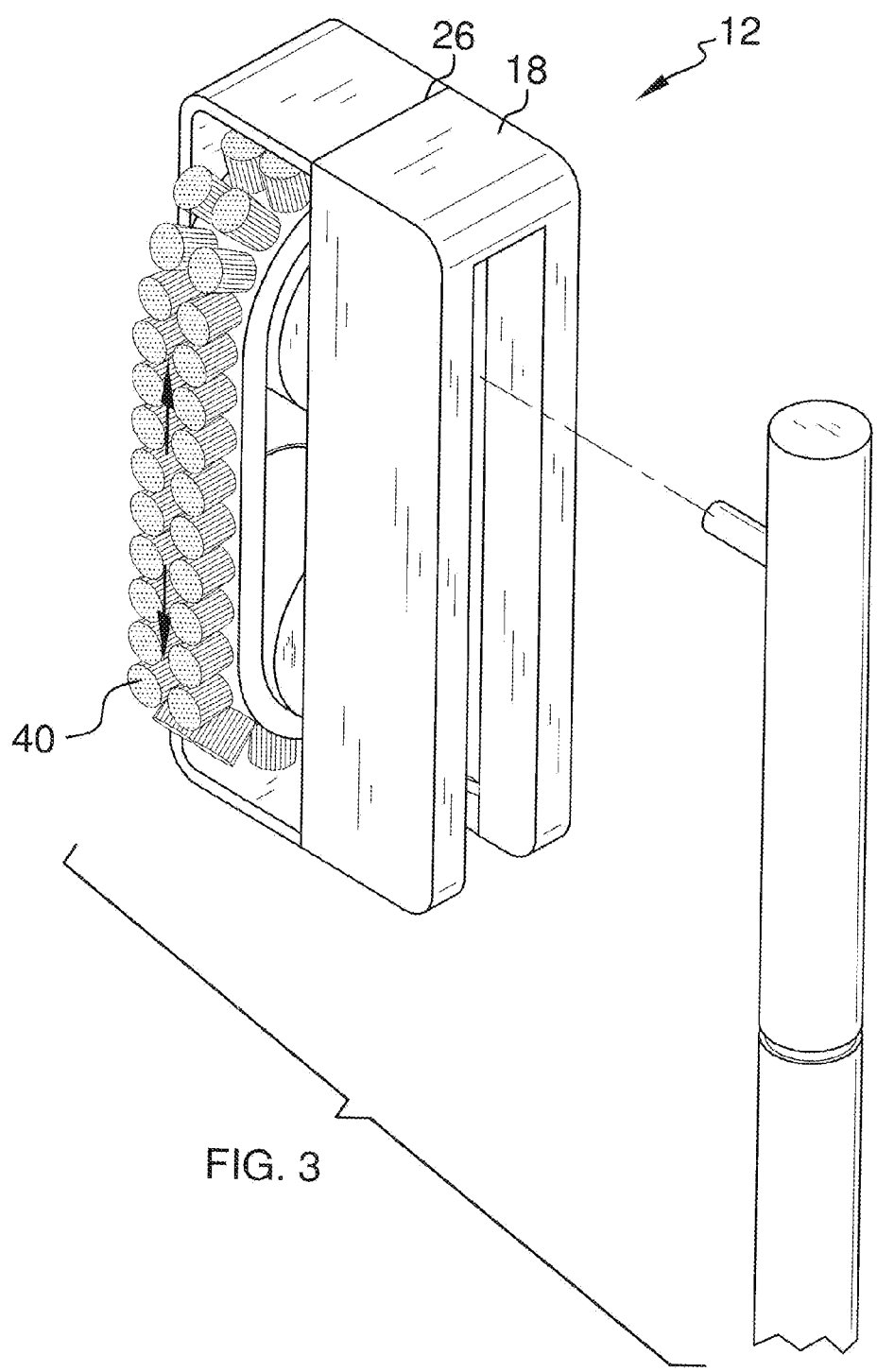
FIG. 3 is a broken right perspective view of an embodiment of the disclosure.
Figure 4:
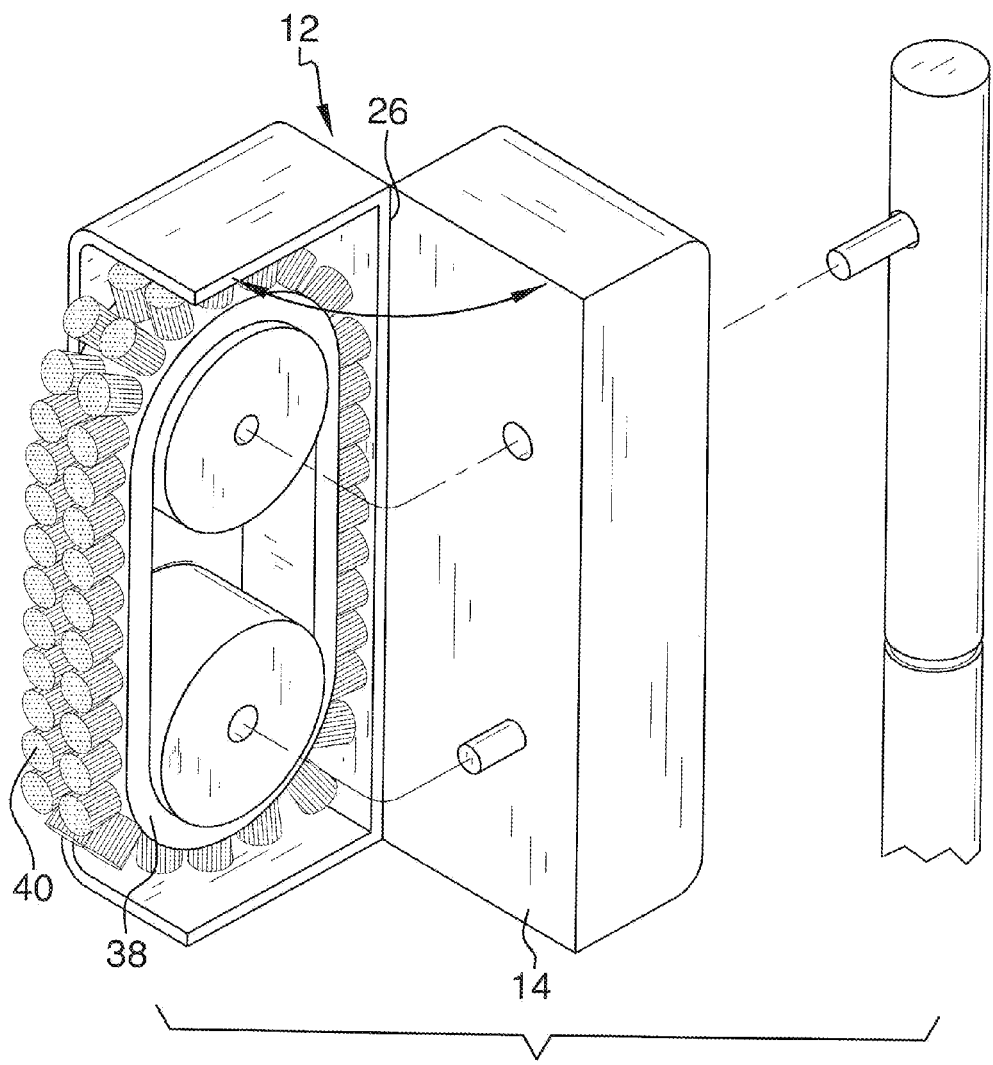
FIG. 4 is a front perspective view of an embodiment of the disclosure.
Figure 5:
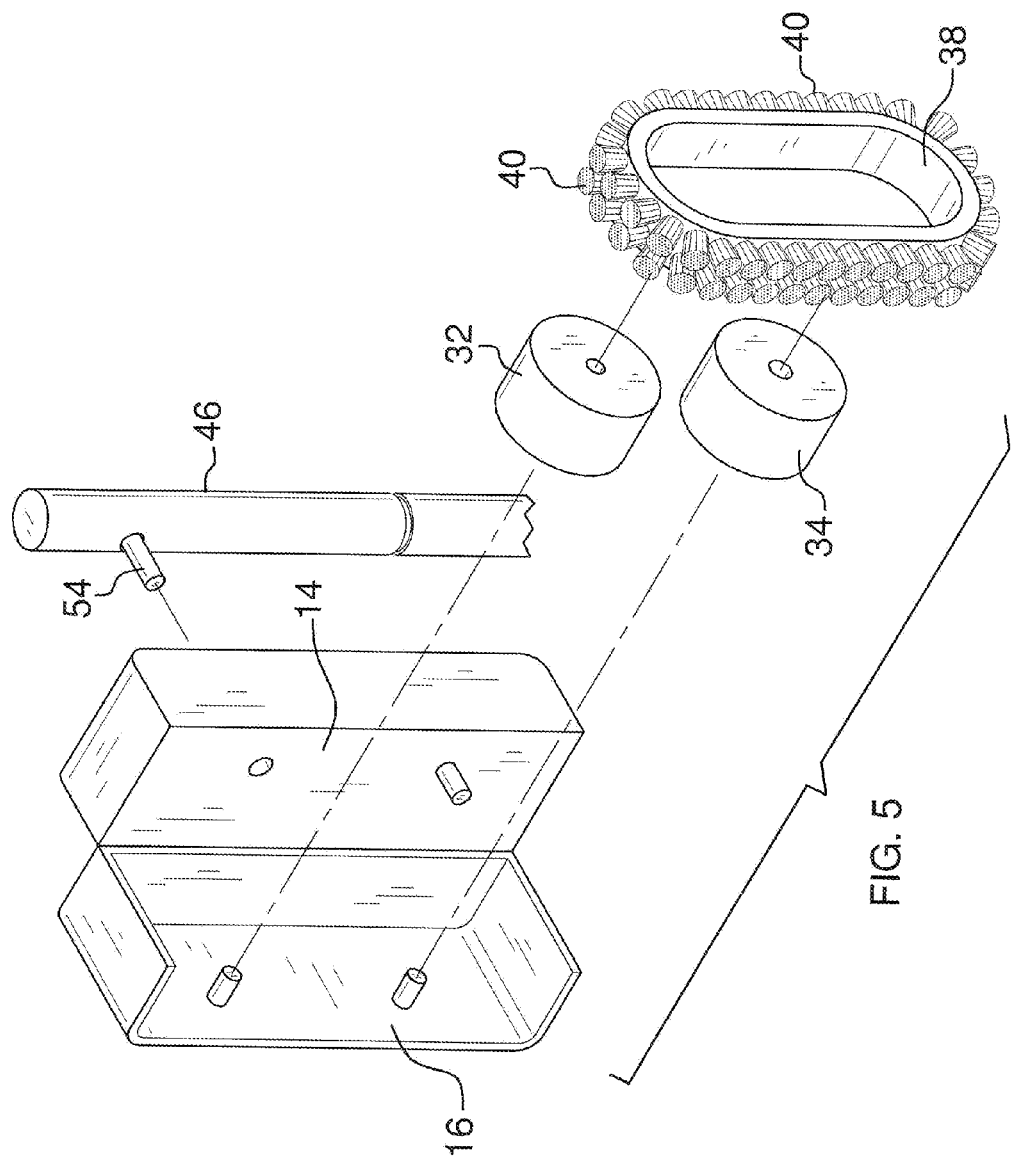
FIG. 5 is a perspective exploded view of an embodiment of the disclosure.

With reference now to the drawings, and in particular to FIGS. 1 through 7 thereof, a new teeth cleaning device embodying the principles and concepts of an embodiment of the disclosure and generally designated by the reference numeral 10 will be described.

As best illustrated in FIGS. 1 through 7, the teeth cleaning assembly 10 generally comprises a housing 12 that has a first wall 14 and a second wall 16 positioned opposite of each other. The housing 12 may further include a top wall 18, a bottom wall 20 and a rear wall 22 wherein a front side 24 of the housing 12 remains open to an interior of the housing 12. The housing 12 may have a break 26 therein to allow easy access into the housing 12. The break 28 may be positioned in the rear wall 22. Moreover, for reasons which will be clear below, the first wall 14 may comprise a compartment having an outer surface 30 having access into the compartment.

Figure 6:
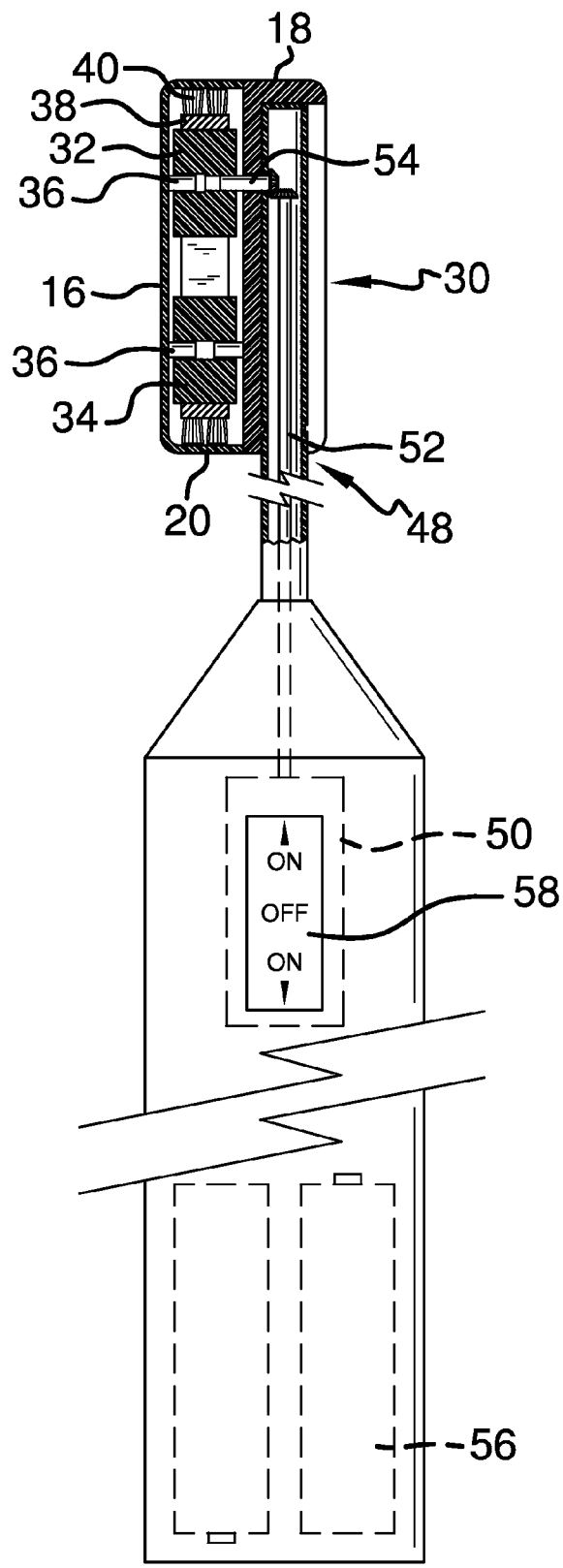
FIG. 6 is a broken front view of an embodiment of the disclosure.
Figure 7:
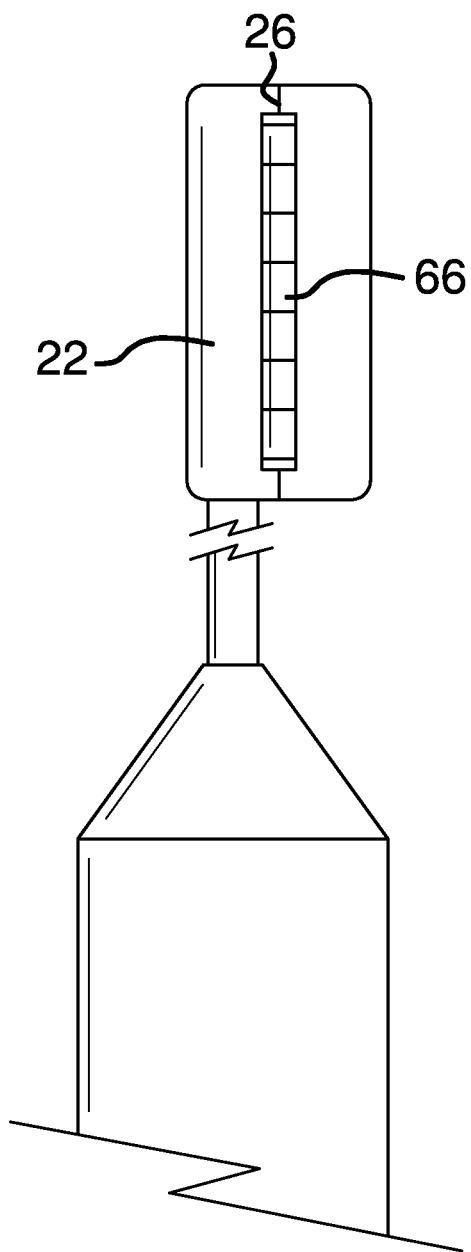
FIG. 7 is a rear view of an embodiment of the disclosure.

A first wheel 32 and a second wheel 34 are provided. Each of the first 32 and second 34 wheels is rotatably mounted in the housing 12. As can be seen in FIG. 6, the first 32 and second 34 wheels have an axis of rotation oriented perpendicular to the first 14 and second 16 walls. Axles 36 or spindles for the first 32 and second 34 wheels may be used to frictionally couple the first 14 and second 16 walls together, though the break 28 may be secured in any conventional manner in a closed condition and a hinge 66 may also be used to couple together sections of the housing 12 formed by the break 26.

A belt 38 is continuous and is positioned on the first 32 and second 34 wheels. The belt 38 is frictionally engaged with the first 32 and second 34 wheels such that the belt 38 rotates the second wheel 34 when the first wheel 32 is rotated. Though not shown, the belt 38 may have alternate configurations such as breaks therein to more easily travel around the first 32 and second 34 wheels, or the first 32 and second 34 wheels may comprise cogs which engage indents or apertures in the belt 38. A plurality or bristles 40 is attached to the belt 38 and extends away from the first 32 and second 34 wheels. The bristles 40 extend outwardly of the front side 24 of the housing 12. The belt 38 is removable from the first 32 and second 34 wheels to allow it to be changed as needed. The first 32 and second 34 wheels each have a diameter being less than 1.5 cm and the bristles 40 each extend outwardly from the belt 38 between 0.5 cm and 2.0 cm A handle 42 is attached to the housing 12. The handle 42 may include a main body 44 and a post 46 extending upwardly from the main body 44. The post 46 has a terminal end with respect to the main body 44 and is extendable into a slot 48 extending into the housing 12. The post 46 may more particularly extend into the compartment of the housing 12. A motor 50 is mounted within the handle 42 and may be positioned in the main body 44. The motor 50 is in mechanical communication with the first wheel 32 such that the motor 50 rotates the first wheel 32 when the motor 50 is energized. This may be achieved with a first drive shaft 52 that is coupled to the motor 50. The first drive shaft 52 extends upwardly through the post 46 to engage a second drive shaft 54 extending through the first wall 14. The second drive shaft 54 is coupled to the first wheel 32 to rotate the first wheel 32 when the motor 50 is energized. The motor 50 is an electric motor and may be powered in any conventional manner such as with batteries 56 which can comprise rechargeable batteries. An actuator 58 is mounted on the handle 42 and is in communication with the motor 50. The actuator 58 is actuated to energize or de-energize the motor.

In use, the assembly 10 is used in a conventional manner to clean a person's teeth. The user will place toothpaste or the like on the bristles 40 and clean their teeth with the bristles 40 while the motor 50 rotates the belt 38 around the first 32 and second 34 wheels. The motor 50 may be a reciprocating motor alternating the rotation of the first drive axle 52 in first and second directions. An alternate construction may include the first wall 14 but not include a second wall 16 such that the bristles 40 are completely exposed as they travel continuously around the first 32 and second 34 wheels.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A toothbrush assembly comprising:
   a housing;
   a first wheel and a second wheel each being rotatably mounted to said housing, said first wheel and said second wheel being coplanar;
   a belt being continuous and being positioned on said first and second wheels, wherein said belt rotates said second wheel when said first wheel is rotated, said belt being oriented to rotate parallel to a longitudinal axis of said housing;
   a plurality of bristles being attached to said belt and extending away from said first and second wheels, said bristles extending outwardly of said housing;
   a handle being attached to said housing, a longitudinal axis of said handle being parallel to a plane in which said first wheel, said second wheel, and said belt are positioned; and
   a motor being mounted within said handle, said motor being in mechanical communication with said first wheel, said motor rotating said first wheel when said motor is energized.

2. The toothbrush assembly according to claim 1, wherein said housing includes a first wall and a second wall positioned opposite of each other, each of said first and second wheels having an axis of rotation oriented perpendicular to said first and second walls.

3. The toothbrush assembly according to claim 1, further including an actuator being mounted on said handle and being in communication with said motor, said actuator being actuated to energize or de-energize said motor.

4. The toothbrush assembly according to claim 1, wherein said handle is removably coupled to said housing.

5. The toothbrush assembly according to claim 4, wherein said handle includes a drive shaft mechanically coupled to said motor, said drive shaft being rotated when said motor is energized, said drive shaft being in mechanical communication with said first wheel when said handle is mounted on said housing.

6. The toothbrush assembly according to claim 1, wherein said belt is removable from said first and second wheels.

7. A toothbrush assembly comprising:
   a housing having a first wall and a second wall positioned opposite of each other;
   a first wheel and a second wheel, each of said first and second wheels being rotatably mounted in said housing, each of said first and second wheels having an axis of rotation oriented perpendicular to said first and second walls, said first wheel and said second wheel being coplanar;
   a belt being continuous and being positioned on said first and second wheels, wherein said belt rotates said second wheel when said first wheel is rotated, said belt being oriented to rotate parallel to a longitudinal axis of said housing;
   a plurality of bristles being attached to said belt and extending away from said first and second wheels, said bristles extending outwardly of said housing;
   a handle being attached to said housing, a longitudinal axis of said handle being parallel to a plane in which said first wheel, said second wheel, and said belt are positioned;
   a motor being mounted within said handle, said motor being in mechanical communication with said first wheel, said motor rotating said first wheel when said motor is energized;
   an actuator being mounted on said handle and being in communication with said motor, said actuator being actuated to energize or de-energize said motor;
   said handle being removably coupled to said housing, said handle including a drive shaft mechanically coupled to said motor, said drive shaft being rotated when said motor is energized, said drive shaft being in mechanical communication with said first wheel when said handle is mounted on said housing; and
   said belt being removable from said first and second wheels.

* * * * *